(12) United States Patent
Landau

(10) Patent No.: US 7,306,109 B2
(45) Date of Patent: Dec. 11, 2007

(54) SYSTEM AND METHOD OF ADMINISTERING PHARMACEUTICALS AND NUTRACEUTICALS AS PART OF A BEVERAGE CONTAINER

(76) Inventor: Steven M Landau, 425 Old York Rd, Jenkintown, PA (US) 19046

( * ) Notice: Subject to any disclaimer, the term of this patent is extended or adjusted under 35 U.S.C. 154(b) by 879 days.

(21) Appl. No.: 10/090,574

(22) Filed: Mar. 5, 2002

(65) Prior Publication Data

US 2003/0170291 A1    Sep. 11, 2003

(51) Int. Cl.
*B65D 39/12* (2006.01)
*B65D 75/00* (2006.01)
*B65D 85/88* (2006.01)
*B65D 65/00* (2006.01)
*A61K 47/00* (2006.01)

(52) U.S. Cl. .................. 215/360; 206/318; 206/524.1; 206/427; 206/445; 206/139; 424/439

(58) Field of Classification Search ................ 424/439; 215/360; 206/318, 524.1, 427, 445, 139
See application file for complete search history.

(56) References Cited

U.S. PATENT DOCUMENTS 5,456,351 A * 10/1995 Johnson
6,527,109 B2 * 3/2003 Schoo et al.

* cited by examiner

*Primary Examiner*—Humera N Sheikh
(74) *Attorney, Agent, or Firm*—LaMorte & Associates

(57) ABSTRACT

A system and method for providing a dry consumable with a liquid in the same assembly. The assembly includes a fluid container that is covered with a cap assembly. The cap assembly can be manually opened and closed, thereby selectively controlling the flow of fluid out of the fluid container. Consumable material is formed into a solid form on the exterior of the cap assembly. The material can include pharmaceutical compounds, nutraceutical compounds or can be inert compounds, such as confections. The material is formed into a solid that can be bitten or licked away from the cap assembly as the cap assembly is placed in the mouth. Once the material is received into the mouth, liquid can be drunk through the cap assembly to help wash the material down the throat.

17 Claims, 5 Drawing Sheets

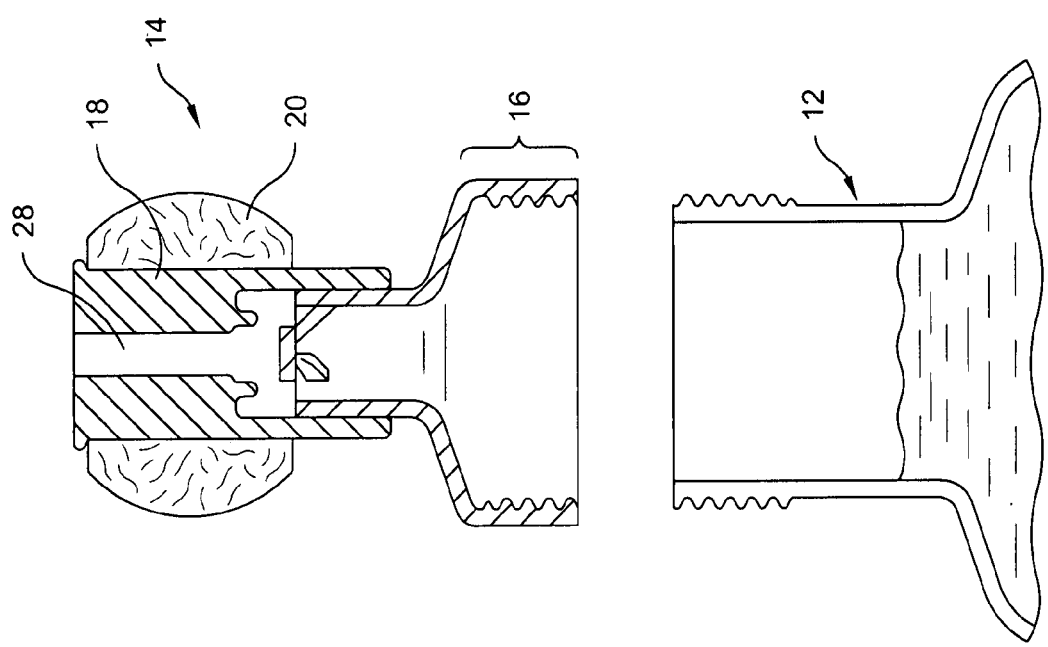

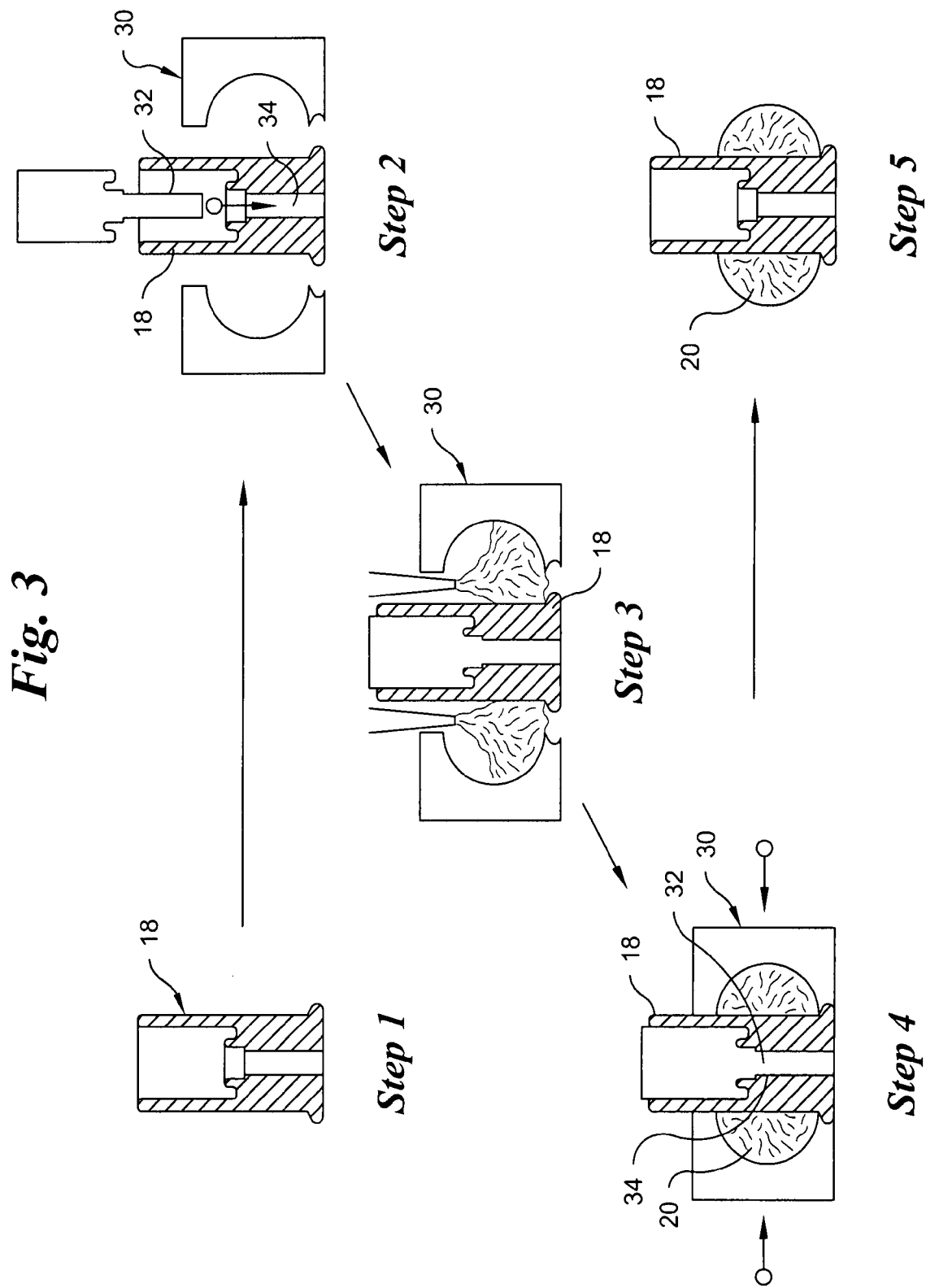

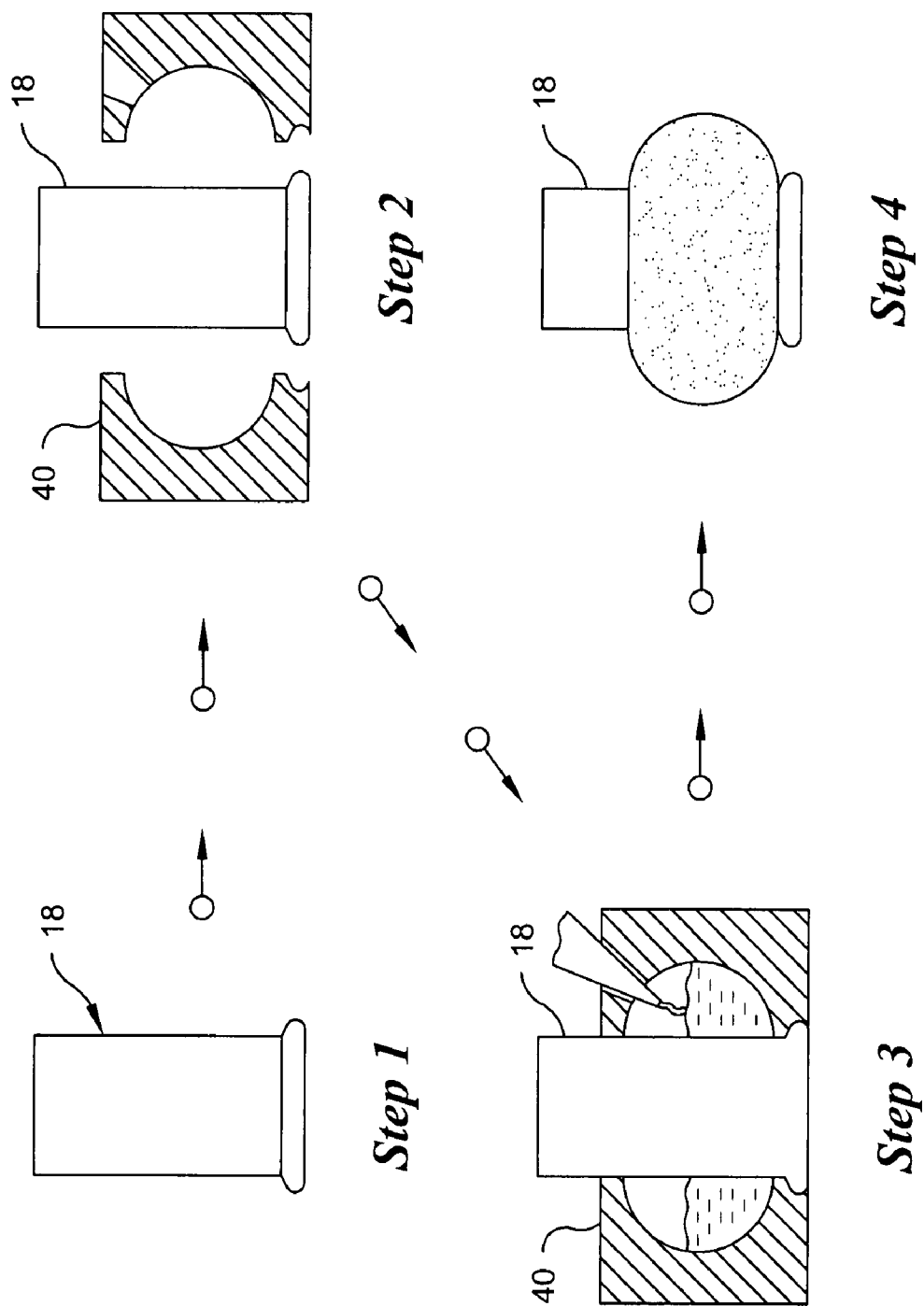

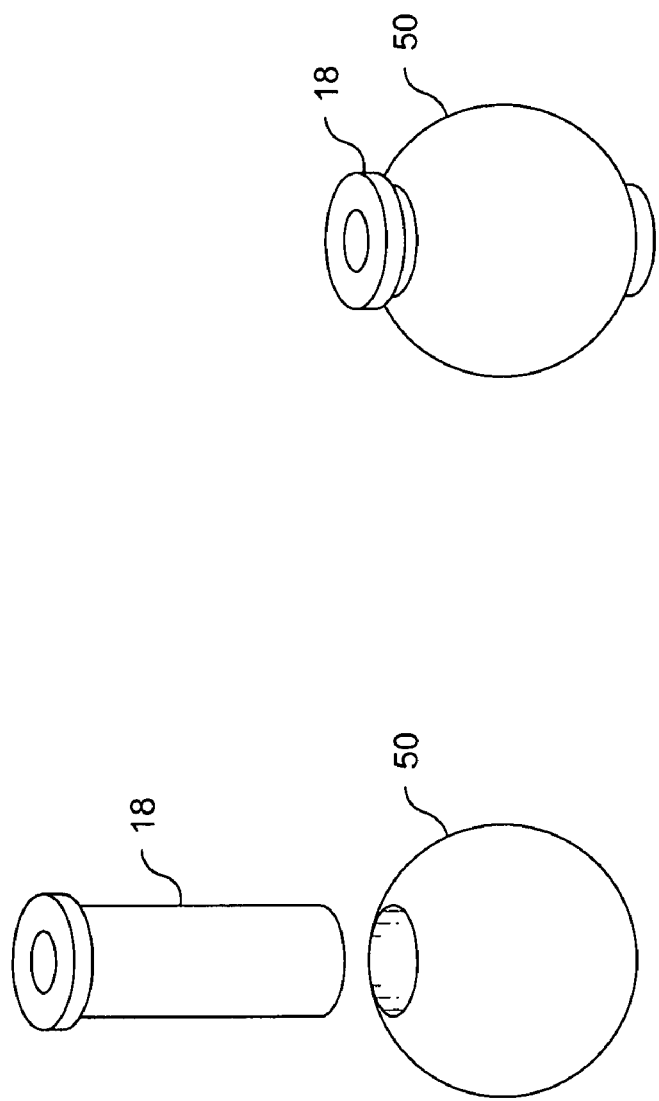

SYSTEM AND METHOD OF ADMINISTERING PHARMACEUTICALS AND NUTRACEUTICALS AS PART OF A BEVERAGE CONTAINER

BACKGROUND OF THE INVENTION

1. Field of the Invention

The present invention relates to beverages and liquids, such as cough syrup, sports drinks, and diet supplement drinks, that contain either pharmaceuticals and/or nutraceuticals. More particularly, the present invention relates to systems that administer pharmaceuticals and/or nutraceuticals that are insoluble in water, incompatible with water, reactive to water or sensitive to heat.

2. Prior Art Statement

The prior art is replete with different types of beverages and other liquids that contain pharmaceuticals or nutraceuticals. For example, many over-the-counter pharmaceuticals, such as cough suppressants, fever reducers, sleeping aids, antacids and the like are sold in liquid suspensions or solutions that are consumed by people. Many commercially available beverages contain nutraceuticals, such as vitamins and minerals. Many popular sports drinks and diet supplement drinks are fortified with proteins, carbohydrates, and electrolytes as well as vitamins, minerals and other nutraceuticals.

Pharmaceuticals themselves rarely have a pleasant taste. By mixing pharmaceuticals into liquids, the flavor of the pharmaceuticals can be altered and made more palatable. Liquids are also more readily swallowed by children than are hard pills. Furthermore, by mixing a pharmaceutical with a liquid, the pharmaceutical also becomes easier to administer in weight sensitive dosages than are hard pills. For example, a child of fifty pounds may need to take one teaspoon of a liquid medication. A child of seventy-five pounds may need to take one and a half teaspoons. If hard pills were used, the pills may have to be cut into sections to provide the same controlled dosages.

By adding nutraceuticals to commercial beverages, the nutritional value of those beverages is increased. For example, by adding electrolytes to sports drinks, athletes are provided with replacement electrolytes that are lost while sweating. The athletes are therefore less likely to develop muscle cramping from a deficiency in electrolytes. Diet supplement drinks can be fortified with various vitamins and minerals that may be lacking in people on a low calorie diet. As such, people who are on diets can drink the diet supplement drink to acquire the vitamins and minerals they would otherwise be lacking.

However, many pharmaceuticals and nutraceuticals are not readily mixed with liquids for a variety of reasons. First, many pharmaceuticals and nutraceuticals are not soluble in water. As such, they are not evenly distributed within a water-based solution. This characteristic is not desirable in either over-the-counter medications or beverages. For example, some calcium salts are not soluble in water. In other cases, the presence of calcium fortification adversely effects the solubility of certain proteins. Second, many pharmaceuticals and nutraceuticals react with water, thereby losing their potency over time. Lastly, many beverages and over-the-counter liquid-based medications are pasteurized. Pasteurization is used to prevent bacterial contamination of the beverage or the medication before that product is sealed in a bottle and sold to the public. However, many pharmaceuticals and nutraceuticals are adversely effected by the heat used during pasteurization. Consequently, the pharmaceuticals and nutraceuticals must be separately sterilized in a low temperature process and mixed with the pre-pasteurized beverage in a separate sterile procedure. This adds greatly to the cost of manufacturing the final consumable product.

A need therefore exists for a system and method of providing a pharmaceutical or nutraceutical with a liquid, without having to mix the pharmaceutical or nutraceutical into the liquid prior to consumption. This need is met by the present invention as described and claimed below.

SUMMARY OF THE INVENTION

The present invention is a system and method for providing a dry consumable with a liquid in the same assembly. The assembly includes a fluid container that is covered with a cap assembly. The cap assembly can be manually opened and closed, thereby selectively controlling the flow of fluid out of the fluid container. Consumable material is disposed in a solid form on the exterior of the cap assembly. The consumable material can include pharmaceutical compounds, nutraceutical compounds or can be inert compounds, such as confections. The material is formed into a solid formation that can be bitten or licked away from the cap assembly as the cap assembly is placed in the mouth. Once the consumable material is taken into the mouth, liquid can be drunk through the cap assembly to help wash the consumable material down the throat.

As such, the present invention provides a single assembly where a person can consume a dry product and be provided with liquid to help swallow that dry product. This system has many uses for people who take pharmaceuticals, nutraceuticals or the like.

BRIEF DESCRIPTION OF THE DRAWINGS

For a better understanding of the present invention, reference is made to the following description of an exemplary embodiment thereof, considered in conjunction with the accompanying drawings, in which:

FIG. 2 is a selectively cross-sectioned view of the cap assembly portion of the beverage container shown in FIG. 1;

FIG. 3 is an exemplary method process schematic illustrating exemplary steps used to manufacture part of the cap assembly portion of the beverage container;

FIG. 4 is an alternate method process schematic illustrating exemplary steps used to manufacture part of the cap assembly portion of the beverage container; and FIG. 5 is another alternate method process schematic illustrating exemplary steps used to manufacture part of the cap assembly portion of the beverage container.

DETAILED DESCRIPTION OF THE INVENTION

Figure 1:
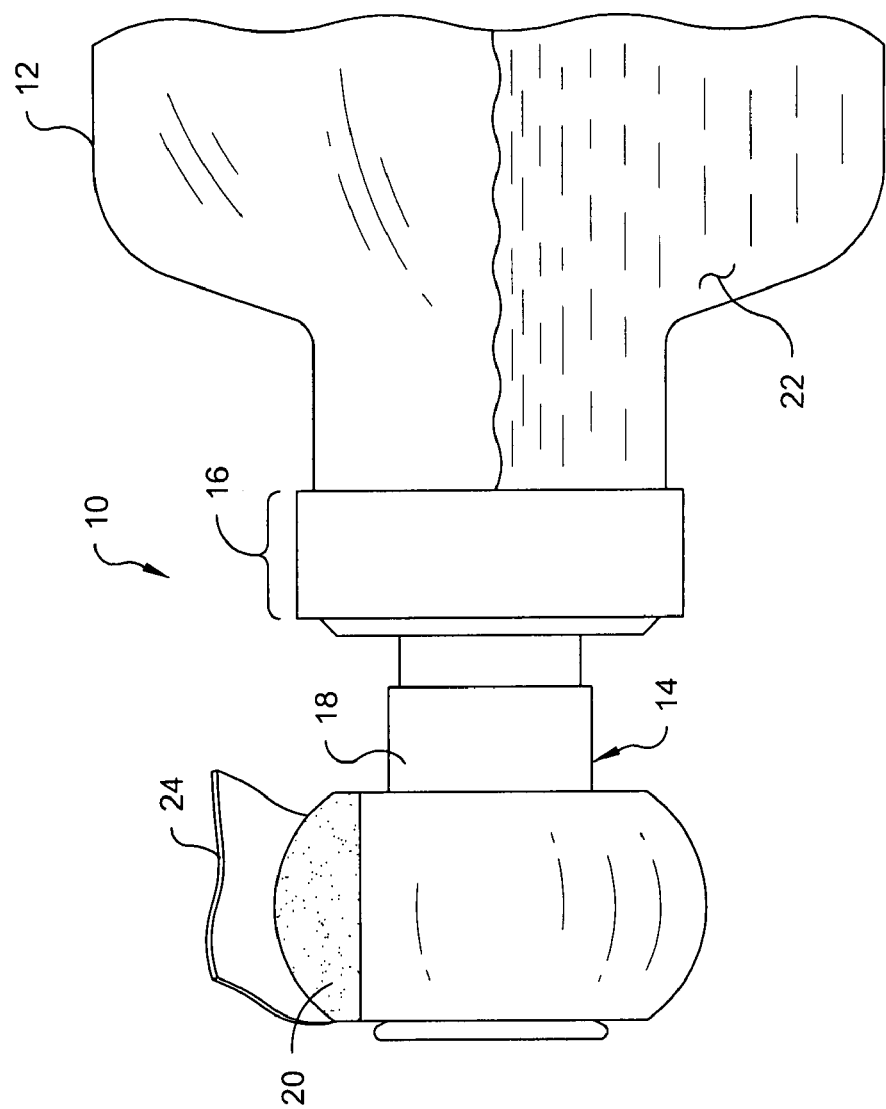
FIG. 1 is a perspective view of an exemplary embodiment of a beverage in accordance with the present invention.

Although the present invention system can be adapted to many different types of beverage containers, the present invention system is especially well suited for use on beverage containers that have cap assemblies that can be selectively opened and closed. As such, by way of example, the present invention system will be described in an application where it is applied to a beverage container having a cap assembly that can be selectively opened and closed by a person drinking from that beverage container in order to set forth the best mode contemplated for the invention.

Referring to FIG. 1, beverage container 10 is shown. The beverage container 10 includes a bottle 12 and a cap assembly 14 threaded onto the neck of the bottle 12. The bottle 12 can be either plastic or glass. The cap assembly 14 obstructs the neck of the bottle 12 and confines the contents of the bottle 12. The cap assembly 14 has a base section 16 that threads onto the neck of the bottle 12 and a closure element 18 that can be manually opened and closed.

Contained in the bottle 12 is a consumable liquid 22. The liquid can be water, milk, a flavored beverage, a nutritional supplement drink or any other liquid consumable that is sold in bottles.

An area of consumable material 20 is present around the closure element 18 on the cap assembly 14. This consumable material 20 is made from powdered biologically beneficial material that is formed into a solid. The biologically beneficial material can be either pharmaceutical compounds that have medicinal uses or nutraceutical compounds that have nutritional uses. The consumable material 20 is protected from the surrounding environment by a protective shrink wrap 24. The protective shrink wrap 24 is perforated for easy removal and can be either transparent or opaque. An opaque shrink wrap material is preferably used, if the consumable material is adversely effected by exposure to light.

The pharmaceutical composition or nutraceutical composition can be any known compositions. However, in the present invention, since the consumable material 20 is held separate from the liquid contents 22 of the bottle 12, the selected pharmaceutical composition or nutraceutical composition is preferably one that is insoluble in liquid, reactive with liquid, adversely effected by being stored in a liquid and/or adversely effected by the pasteurization of the liquid. Consequently, by keeping the consumable material 20 away from the liquid contents 22 of the bottle 12, the liquid contents 22 and consumable material 20 can be manufactured using separate processes. Furthermore, the consumable material 20 will experience no adverse effects from the liquid contents 22, since the compacted material 20 is not mixed with the liquid contents 22.

The consumable material 20 on the cap assembly 14 can be formed in many ways. In one method, the consumable material 20 is compacted into a lightly packed solid. As such, the consumable material 20 is not hard and easily crumbles when stressed. A person can therefore place the consumable material 20 into their mouths and lightly bite the consumable material 20. When the compacted consumable material 20 is bitten, it will break apart from its compacted form and fall away from the remainder of the cap assembly 14. Since the consumable material 20 is in the mouth when bitten from the cap assembly 14, the broken consumable material 20 falls into the mouth for consumption. Furthermore, since the cap assembly 14 of the beverage container 10 is in the mouth as the consumable material 20 is bitten away, a person can drink the liquid contents 22 through the cap assembly 14 and wash the consumable material 20 down the throat.

Some simple examples of applications of the present invention, are as follows. The beverage container 10 can have a bottle 12 filled with several ounces of water. The consumable material 20 on the cap assembly 14 can be aspirin or acetaminophen. The beverage container 10 can be sold as a headache kit. A person can buy the beverage container 10, remove the protective shrink wrap 24, bite away the medication and wash it down with the water in the bottle.

A person with the AIDS virus, who is on a strictly regimented program of medications, can buy beverage containers specifically manufactured with the appropriate AIDS treatment drugs. That person can then conveniently take the drugs without having to swallow the medication dry or go and find a beverage with which to wash the pills down.

An athlete, who wants to take a protein supplement that is not soluble in water, can purchase specially manufactured beverage containers containing a compacted protein supplement on the cap assembly. The beverage container can be filled with water or a sports drink to help wash the protein supplement down.

Referring to FIG. 2, it can be seen that the cap assembly 14 has a base section 16 that engages the threaded neck of a bottle 12. Flow through the cap assembly 14 is controlled by a closure element 18. The consumable material 20 is manufactured around the exterior of the closure element 18. The closure element 18 itself is molded plastic or an elastomeric material. The structure of the closure element 18 is elongated. As such, the closure element 18 protrudes from the top of the cap assembly 14. Part of the closure element 18 that protrudes from the remainder of the cap assembly 14 is surrounded by the consumable material 20. Since the closure element 18 is elongated, the presence of the consumable material 20 does not effect the function of the closure element 18 when the closure element 18 is either manually opened or closed. The elongated closure element 18 also assists with the placement of the closure element 18 in the mouth. Many people have brittle teeth and do not like to bite onto objects with their front teeth. By having an elongated closure element 18, the compacted material 20 can be readily engaged in the mouth by a person's molars.

From FIG. 2, it can be seen that the closure element 18 has a tubular body that defines a central fluid conduit 28. When the closure element 18 is in its depressed closed position, the central fluid conduit 28 is blocked. When the closure element 18 is pulled up, fluid from the bottle 12 is free to pass through the central fluid conduit 28. In FIG. 2, the closure element 18 in the cap assembly 14 is shown in its open configuration. From FIG. 2, it can also be seen that the consumable material 20 is formed around a section of the closure element 18. The section of the closure element 18 surrounded by the consumable material 20 remains exposed regardless of whether the closure element 18 is in its open position or closed position.

The closure element 18 preferably has a color that is highly contrasting to the color of the consumable material 20. In this manner, a person lightly sucking on the consumable material will know when a full dosage has been received. A full dosage is received, when the color of the consumable material 20 is no longer present and only the color of the underlying consumable material remains.

Referring now to FIG. 3, one exemplary method of making the closure element 14 of the cap assembly is shown. In this method the consumable material is fabricated from a compacted powder. In Step 1, a plastic or elastomeric closure element 18 is provided. Such a closure element 18 is molded using traditional injection molding techniques. In Step 2, the closure element 18 is placed into a molding press 30. The molding press 30 has a central shaft 32 that extends through the fluid aperture 34 in the closure element 18. The molding press 30 has a shaped molding face that surrounds the portion of the closure element 18 that will be covered with the consumable material.

In Step 3, a measured amount of powdered pharmaceutical compound or nutraceutical compound is added to the molding press 30 around the closure element 18. Alternatively, a liquefied compound that cures or dries can also be used in place of powdered material. The pharmaceutical compound can be any compound that has medicinal properties. The nutraceutical compound can be any compound that can be produced in a powder and has nutritional properties.

In Step 4, the molding press 30 closes around the closure element 18. The closing of the molding press 30 compacts the pharmaceutical or nutraceutical material and forms a mass of compressed consumable material 20 around the closure element 18. As the molding press 30 closes and compresses the biologically beneficial material, the closure element 18 is also compressed. The presence of the shaft 32 in the fluid conduit 34 of the closure element 18 prevents the closure element 18 from collapsing under the force of the molding press 30. The force used to compress the biologically beneficial material is sufficient to compress that material into a loosely compacted solid. However, that force is not sufficient to damage the plastic structure of the closure element 18 once it is reinforced by the shaft 32.

In Step 5, the molding press 30 is removed, thereby leaving the closure element 18 with the compacted consumable material 20 formed as a solid ring around the closure element 18. The closure element 18 can then be assembled into the cap assembly 10 (FIG. 1). If the cap assembly manufacturing procedure stresses the closure element 18 and causes breakage of the compressed consumable material 20, the closure element 18 can first be added to the cap assembly 10 (FIG. 1) before the compacted consumable material 20 is added to the closure element.

Referring to FIG. 4, an alternate method of manufacture is shown. In this method, the closure element 18 of a cap assembly 14 (FIG. 1) is provided and is placed in a mold 40. See Step 1 and Step 2. The mold 40 is then filled with a molten solution containing the biologically beneficial material. See Step 3. As the molten solution cools in the mold, the material cures and becomes solid. As is indicated by Step 4, once the biologically beneficial material solidifies, the mold 40 is removed.

Referring to FIG. 5, another alternate method of manufacture is shown. In this embodiment, an annular body 50 of biologically beneficial material is manufactured using known molding or compression techniques. See Step 1. The annular body is then advanced over the closure element 18 of a cap assembly 14. See Step 2.

It will be understood that the present invention system and method of manufacture that are described and illustrated are merely exemplary and a person skilled in the art can make many variations to the shown embodiment. For example, the shape and style of the cap assembly shown in the illustrations can be changed as desired. The pharmaceutical compounds and nutraceutical compounds referenced in earlier examples are merely exemplary and can be changed to include most any pharmaceutical or nutraceutical. All such alternate embodiments and modifications are intended to be included within the scope of the present invention as defined below in the claims.

What is claimed is:

1. A method of administering a biologically beneficial compound, comprising the steps of:
   providing a beverage container having a cap assembly through which liquid in said beverage container is drunk, wherein said cap assembly has at least one exterior surface that passes into a drinker's mouth when said liquid is drunk through said cap assembly;
   forming a mass of a biologically beneficial compound on said at least one exterior surface of said cap assembly, wherein said mass of biologically beneficial compound passes into the mouth of a person drinking from said beverage container through said cap assembly.

2. The method according to claim 1, further including the step of providing a removable protective cover around said mass of biologically beneficial material.

3. The method according to claim 1, wherein said step of forming a mass includes compacting a powdered material into a solid form.

4. The method according to claim 3, wherein said powdered material is compacted into said solid form directly upon said at least one exterior surface of said cap assembly.

5. The method according to claim 3, wherein said powdered material is compacted into said solid form and is then attached to said at least one exterior surface of said cap assembly.

6. The method according to claim 1, wherein said step of forming a mass includes molding molten material around said at least one exterior surface of said cap assembly and allowing said molten material to solidify.

7. The method according to claim 1, wherein said step of forming a mass includes forming an annular structure, and said method includes attaching said annular structure to said at least one exterior surface of said cap assembly.

8. The method according to claim 1, wherein said biologically beneficial material is selected from a group consisting of pharmaceuticals and nutraceuticals.

9. The method according to claim 1, wherein said step of forming a mass includes the substeps of:
   placing at least a segment of said cap assembly in a press;
   placing powdered biologically beneficial material in said press; and
   compressing said powdered biologically beneficial material into a solid form around said segment of said cap assembly.

10. The method according to claim 1, further including a liquid in said beverage container that can be drunk through the cap assembly of said beverage container, wherein said biologically beneficial material is not completely soluble in said liquid.

11. The method according to claim 1, further including a liquid in said beverage container that can be drunk through the cap assembly of said beverage container, wherein said biologically beneficial material is adversely effected over time when mixed with said liquid.

12. A method, comprising the steps of:
   providing a bottle containing a consumable liquid;
   providing a cap assembly for said bottle, wherein said cap assembly has at least one exterior surface and wherein said cap assembly can be selectively opened and said consumable liquid drunk from said bottle through said cap assembly;
   providing a consumable material on said at least one exterior surface of said cap assembly, wherein said consumable material passes into the mouth when said consumable liquid is drunk directly from said cap assembly.

13. The method according to claim 12, wherein said step of providing a consumable material includes compressing powdered material into a solid form on said at least one exterior surface of said cap assembly.

14. The method according to claim 12, wherein said step of forming a mass includes molding molten material around said at least one exterior surface of said cap assembly and allowing said molten material to solidify.

15. The method according to claim 12, wherein said step of forming a mass includes forming an annular structure, and said method includes attaching said annular structure to said at least one exterior surface of said cap assembly.

16. The method according to claim 12, wherein said consumable material is selected from a group consisting of pharmaceutical compounds and nutraceutical compounds.

17. The method according to claim 12, wherein said consumable material is not completely soluble in said consumable liquid.

* * * * *